(12) United States Patent
Levy (10) Patent No.: US 7,041,644 B2
(45) Date of Patent: *May 9, 2006

(54) THERAPEUTIC USES OF BPI PROTEIN PRODUCTS IN BPI-DEFICIENT HUMANS

(75) Inventor: Ofer Levy, Boston, MA (US)

(73) Assignee: XOMA Technology, Berkeley, CA (US)

(*) Notice: Subject to any disclaimer, the term of this patent is extended or adjusted under 35 U.S.C. 154(b) by 157 days.

This patent is subject to a terminal disclaimer.

(21) Appl. No.: 10/128,139

(22) Filed: Apr. 23, 2002

(65) Prior Publication Data

US 2003/0027762 A1 Feb. 6, 2003

Related U.S. Application Data

(63) Continuation-in-part of application No. 09/541,821, filed on Apr. 3, 2000, now Pat. No. 6,376,465, which is a continuation-in-part of application No. 09/285,124, filed on Apr. 1, 1999, now Pat. No. 6,153,584.

(51) Int. Cl.
*A61K 38/00* (2006.01)

(52) U.S. Cl. ............................................. 514/12; 514/2

(58) Field of Classification Search ................ 514/172, 514/2
See application file for complete search history.

(56) References Cited

U.S. PATENT DOCUMENTS

| | | | | |
|---|---|---|---|---|
| 5,827,816 A | | 10/1998 | Theofan et al. ................. | 514/2 |
| 6,153,584 A | * | 11/2000 | Levy ............................ | 514/12 |
| 6,376,465 B1 | * | 4/2002 | Levy ............................ | 514/12 |

FOREIGN PATENT DOCUMENTS

WO WO 89/01486 2/1989
WO WO 98/06415 2/1989

OTHER PUBLICATIONS

Elsbach "The ba ctericidal/permeability-increasing protein (BPI) in antibacterial host defense " *Jou. of Leukocyte Bio.* 64:14-18 (1998).
Levy et al., "Impaired Inn ate Immunity in the Newborn: Newborn Neutrophils are Deficient in Bactericidal/Permeability-Increasing Protein" *Pediatrics* 104:1327-1333 (1999).
Wong et al., "Plasma Bactericidal/Permeability-Increasing Protein Concentrations in Critically Ill Children with the Sepsis Syndrome," *Pediatr. Dis. J.*, 14:1087-1097 (1995).
Anonymous, "Supplementation and Plasma Levels of Vitamin A in Premature Newborns at Risk for Chronic Ling Disease. Italian Collaborative Group on Preterm Delivery (ICGPD)," *Dev. Pharm. and Therapeutics*, 20:144-151 (1993).
Sands et al., "Epidemiology of Sepsis Syndrome in 8 Academic Medical Centers, " *JAMA*, 278:234-240 (1997).
McCourt M., "At Risk for Infection: The Very Low Birthweight Infant," *J of Perinatal and Neonatal Nursing*, 7:52-64 (1994).
Ammons et al., "An N-Terminal Fragment od Bactericidal/Permeability-Increasing Protein Protects Against Hemodynamic and Metabolic Derangements in Rat Gram-Negative Species," *J. Endotoxin Res.*, 3:57-66 (1996).

* cited by examiner

*Primary Examiner*—Robert A. Wax
*Assistant Examiner*—Suzanne M. Mayer
(74) *Attorney, Agent, or Firm*—Anne Dollard; Lily Rin Laures (57) ABSTRACT

New therapeutic uses for BPI protein products that involve treatment of subjects with a BPI deficiency condition, including selective BPI deficiency, and newborns, including BPI-deficient newborns.

22 Claims, 1 Drawing Sheet

FIGURE 1

SEQUENCE LISTING

```
<160> NUMBER OF SEQ ID NOS: 2

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<220> FEATURE:
<221> NAME/KEY: mat_peptide
<222> LOCATION: (124)..(1491)

<400> SEQUENCE: 1
caggccttga ggttttggca gctctggagg atg aga gag aac atg gcc agg ggc      54
                                 Met Arg Glu Asn Met Ala Arg Gly
                                 -30                 -25 cct tgc aac gcg ccg aga tgg gtg tcc ctg atg gtg ctc gtc gcc ata     102
Pro Cys Asn Ala Pro Arg Trp Val Ser Leu Met Val Leu Val Ala Ile
```

-continued

|  |  |  |  |  |  |  |  |  |  |  |  |  |  |  |  |
|---|---|---|---|---|---|---|---|---|---|---|---|---|---|---|---|
| ggc | acc | gcc | gtg | aca | gcg | gcc | gtc | aac | cct | ggc | gtg | gtc | agg | atc | 150 |
| Gly | Thr | Ala | Val | Thr | Ala | Ala | Val | Asn | Pro | Gly | Val | Val | Arg | Ile |  |
|  | -5 |  |  |  | -1 | 1 |  |  |  | 5 |  |  |  |  |  |
| tcc | cag | aag | ggc | ctg | gac | tac | gcc | agc | cag | cag | ggg | acg | gcc | gct | ctg | 198 |
| Ser | Gln | Lys | Gly | Leu | Asp | Tyr | Ala | Ser | Gln | Gln | Gly | Thr | Ala | Ala | Leu |
| 10 |  |  |  |  | 15 |  |  |  |  | 20 |  |  |  |  | 25 |

(Gene sequence table continues with columns: nucleotide triplets, amino acid codes, position numbers, and cumulative length.)

cag aag gag ctg aag agg atc aag att cct gac tac tca gac agc ttt    246
Gln Lys Glu Leu Lys Arg Ile Lys Ile Pro Asp Tyr Ser Asp Ser Phe
              30                  35                  40 aag atc aag cat ctt ggg aag ggg cat tat agc ttc tac agc atg gac    294
Lys Ile Lys His Leu Gly Lys Gly His Tyr Ser Phe Tyr Ser Met Asp
              45                  50                  55 atc cgt gaa ttc cag ctt ccc agt tcc cag ata agc atg gtg ccc aat    342
Ile Arg Glu Phe Gln Leu Pro Ser Ser Gln Ile Ser Met Val Pro Asn
              60                  65                  70 gtg ggc ctt aag ttc tcc atc agc aac gcc aat atc aag atc agc ggg    390
Val Gly Leu Lys Phe Ser Ile Ser Asn Ala Asn Ile Lys Ile Ser Gly
        75                  80                  85 aaa tgg aag gca caa aag aga ttc tta aaa atg agc ggc aat ttt gac    438
Lys Trp Lys Ala Gln Lys Arg Phe Leu Lys Met Ser Gly Asn Phe Asp
90                  95                 100                 105 ctg agc ata gaa ggc atg tcc att tcg gct gat ctg aag ctg ggc agt    486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc    534
Asn Pro Thr Ser Gly Lys Pro Thr Ile Thr Cys Ser Ser Cys Ser Ser
        125                 130                 135 cac atc aac agt gtc cac gtg cac atc tca aag agc aaa gtc ggg tgg    582
His Ile Asn Ser Val His Val His Ile Ser Lys Ser Lys Val Gly Trp
        140                 145                 150 ctg atc caa ctc ttc cac aaa aaa att gag tct gcg ctt cga aac aag    630
Leu Ile Gln Leu Phe His Lys Lys Ile Glu Ser Ala Leu Arg Asn Lys
        155                 160                 165 atg aac agc cag gtc tgc gag aaa gtg acc aat tct gta tcc tcc aag    678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct    726
Leu Gln Pro Tyr Phe Gln Thr Leu Pro Val Met Thr Lys Ile Asp Ser
                190                 195                 200 gtg gct gga atc aac tat ggt ctg gtg gca cct cca gca acc acg gct    774
Val Ala Gly Ile Asn Tyr Gly Leu Val Ala Pro Pro Ala Thr Thr Ala
        205                 210                 215 gag acc ctg gat gta cag atg aag ggg gag ttt tac agt gag aac cac    822
Glu Thr Leu Asp Val Gln Met Lys Gly Glu Phe Tyr Ser Glu Asn His
        220                 225                 230 cac aat cca cct ccc ttt gct cca cca gtg atg gag ttt ccc gct gcc    870
His Asn Pro Pro Pro Phe Ala Pro Pro Val Met Glu Phe Pro Ala Ala
235                 240                 245 cat gac cgc atg gta tac ctg ggc ctc tca gac tac ttc ttc aac aca    918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga    966
Ala Gly Leu Val Tyr Gln Glu Ala Gly Val Leu Lys Met Thr Leu Arg
                270                 275                 280 gat gac atg att cca aag gag tcc aaa ttt cga ctg aca acc aag ttc   1014
Asp Asp Met Ile Pro Lys Glu Ser Lys Phe Arg Leu Thr Thr Lys Phe
        285                 290                 295 ttt gga acc ttc cta cct gag gtg gcc aag aag ttt ccc aac atg aag   1062

-continued

```
                Phe Gly Thr Phe Leu Pro Glu Val Ala Lys Lys Phe Pro Asn Met Lys
                    300                 305                 310 ata cag atc cat gtc tca gcc tcc acc ccg cca cac ctg tct gtg cag        1110
Ile Gln Ile His Val Ser Ala Ser Thr Pro Pro His Leu Ser Val Gln
    315                 320                 325 ccc acc ggc ctt acc ttc tac cct gcc gtg gat gtc cag gcc ttt gcc        1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac        1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga        1254
Thr Thr Gly Ser Met Glu Val Ser Ala Glu Ser Asn Arg Leu Val Gly
            365                 370                 375 gag ctc aag ctg gat agg ctc ctc ctg gaa ctg aag cac tca aat att        1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta        1350
Gly Pro Phe Pro Val Glu Leu Leu Gln Asp Ile Met Asn Tyr Ile Val
    395                 400                 405 ccc att ctt gtg ctg ccc agg gtt aac gag aaa cta cag aaa ggc ttc        1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag        1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa            1491
Pro His Gln Asn Phe Leu Leu Phe Gly Ala Asp Val Val Tyr Lys
                445                 450                 455 tgaaggcacc agggtgccg gggctgtca gccgcacctg ttcctgatgg gctgtggggc       1551
accggctgcc tttccccagg gaatcctctc cagatcttaa ccaagagccc cttgcaaact    1611
tcttcgactc agattcagaa atgatctaaa cacgaggaaa cattattcat tggaaaagtg    1671
catggtgtgt attttaggga ttatgagctt cttcaagggg ctaaggctgc agagatattt    1731
cctccaggaa tcgtgtttca attgtaacca agaaatttcc atttgtgctt catgaaaaaa    1791
aacttctggt tttttttcatg tg                                              1813
```

<210> SEQ ID NO 2
<211> LENGTH: 487
<212> TYPE: PRT
<213> ORGANISM: Homo sapiens

<400> SEQUENCE: 2

```
Met Arg Glu Asn Met Ala Arg Gly Pro Cys Asn Ala Pro Arg Trp Val
    -30                 -25                 -20

Ser Leu Met Val Leu Val Ala Ile Gly Thr Ala Val Thr Ala Ala Val
-15                 -10                  -5                  -1   1

Asn Pro Gly Val Val Arg Ile Ser Gln Lys Gly Leu Asp Tyr Ala
                5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
    50                  55                  60                  65

Ser Gln Ile Ser Met Val Pro Asn Val Gly Leu Lys Phe Ser Ile Ser
                70                  75                  80
```

```
Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
            115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
                165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
            195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
            310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
            355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
            435                 440                 445

Gly Ala Asp Val Val Tyr Lys
450                 455
```

THERAPEUTIC USES OF BPI PROTEIN PRODUCTS IN BPI-DEFICIENT HUMANS

This application is a continuation-in-part of U.S. application Ser. No. 09/541,821, filed Apr. 3, 2000, now U.S. Pat. No. 6,376,465, issued Apr. 23, 2002, which is a continuation-in-part of U.S. application Ser. No. 09/285,124 filed Apr. 1, 1999, now U.S. Pat. No. 6,153,584 issued Nov. 11, 2000, both which are incorporated herein by reference.

FIELD OF THE INVENTION

The present invention relates generally to novel therapeutic uses of BPI protein products that involve treatment of BPI-deficient subjects.

BACKGROUND OF THE INVENTION

Newborns as a group are at increased risk for invasive bacterial infections and resulting sepsis. Although the majority of these infections in newborns are caused by gram-positive organisms, a variable but significant percentage of bacterial infections (about 20–40%) are due to gram-negative bacteria, particularly *E. coli*, *Haemophilus influenzae*, *Klebsiella* spp., and *Enterobacter* spp. In fact, it is the gram-negative infections that are, in some studies, associated with the highest mortality rate, which can be as high as about 40%. [Beck-Sague, C M et al., *Pediatr Infect Dis J* 13: 1110–116 (1994) and Stoll, B J et al., *J Pediatr* 129: 63–71 (1996)]

The mechanisms by which newborns are at increased risk for these bacterial infections are not currently understood. Although the neutrophil defense system is innate, there are indications that its function at birth is immature and suboptimal. Previous investigations of the activity of newborn neutrophils have demonstrated impaired adherence, chemotaxis, and phagocytosis. [Wright W C Jr. et al. *Pediatrics* 56: 579–584 (1975); Cairo M S, *AJDC*, 143:40–46 (1989); Schelonka R L et al., *Sem. Perinatol.*, 22:2–14 (1998).] Impaired stimulus-induced adhesion and migration has been associated with decreased surface expression of L-selectin and the $\beta_2$-integrin Mac-1. [Dinauer, M C, in "Hematology of Infancy & Childhood," 5th ed., Nathan and Orkin, eds., Vol I, pp 889–967 (1998)] These findings may explain the difficulty in mobilizing neutrophils to sites of bacterial infection but do not explain the decreased phagocytic and bactericidal activity of the neutrophils of newborns.

Most studies of the microbicidal mechanism of new born neutrophils have focused on the oxidative mechanism (i.e., the phagocyte oxidase/MPO/hydroxyl radical system), with conflicting data indicating either increased or decreased capacity of this oxygen-dependent mechanism in newborns. [Dinauer, supra, and Ambruso et al., *Ped Res* 18:1148–53 (1984).] Despite a growing literature on antibiotic proteins and peptides, little is known about the oxygen-independent microbicidal mechanisms of newborn neutrophils. A slightly decreased content of specific (secondary) granules in the neutrophils of newborns has been documented, with an associated modest ($\leq$ 2-fold) decrease in lysozyme and lactoferrin content relative to adult neutrophils. [Ambruso et al., supra.] However, the major elements of the oxygen-independent antimicrobial arsenal of neutrophil primary granules, including BPI and the defensin peptides, have not been assessed in neonates. Qing et al., *Infect. Immun.*, 64:4638–4642 (1996), compared the lipopolysaccharide (LPS) binding of newborn neutrophils to that of adult neutrophils and reported that the newborn neutrophils have lower levels of membrane-associated 55–57 kDa and 25 kDa proteins capable of binding LPS. Although the missing proteins were not identified, the size and binding properties of the 55–57 kDa protein appeared to be similar to those of bactericidal/permeability-increasing protein (BPI) and the surface LPS receptor CD14.

The rising tide of antibiotic resistance has placed renewed emphasis on the development of agents to treat bacterial infection and its sequelae. Moreover, improved technology has led to increased survival rates for extremely ill full-term as well as premature neonates, which represent a growing population at high risk for bacterial infection. Although the replacement of neutrophils by granulocyte transfusion in newborns with sepsis has apparently been beneficial in some studies [Cairo et al., *Pediatrics* 74: 887–92 (1984)] this potential therapy has been complicated by difficulty in obtaining histocompatible neutrophils and by transfusion reactions.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254: 11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. nucleic acid and amino acid sequences are set out in SEQ ID NOS: 1 and 2 hereto. U.S. Pat. Nos. 5,198,541 and 5,641,874 discloses recombinant genes encoding and methods for expression of BPI proteins, including BPI holoprotein and fragments of BPI. Recombinant human BPI holoprotein has also been produced in which valine at position 151 is specified by GTG rather than GTC, residue 185 is glutamic acid (specified by GAG) rather than lysine (specified by AAG) and residue 417 is alanine (specified by GCT) rather than valine (specified by GTT).

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays some endotoxin-neutralizing activity and only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. [Gazzano-Santoro et al., *Infect. Immun.* 60:4754–4761 (1992).] An N-terminal analog of BPI, designated rBPI$_{21}$ [rBPI(1–193)ala$^{132}$], has been produced as described in U.S. Pat. No. 5,420,019 and Horwitz et al., *Protein Expression Purification*, 8:28–40 (1996). An additional N-terminal analog of BPI, designated rBPI (10–193)C132A or rBPI(10–193)ala$^{132}$, has been produced as described in U.S. Pat. No. 6,013,631.

The bactericidal effect of BPI was originally reported to be highly specific to gram-negative species, e.g., in Elsbach and Weiss, *Inflammation: Basic Principles and Clinical Correlates*, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI protein products have a wide variety of beneficial activities. BPI protein products are bactericidal for gram-negative bacteria, as described in U.S. Pat. Nos. 5,198,541, 5,641,874, 5,948,408, 5,980,897 and 5,523,288. International Publication No. WO 94/20130 proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. Nos. 5,948,408, 5,980,897 and 5,523,288 and International Publication Nos. WO 89/01486 (PCT/US99/02700) and WO 95/08344 (PCT/US94/11255). BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656). BPI protein products exhibit antifungal activity, and enhance the activity of other antifungal agents, as described in U.S. Pat. No. 5,627,153 and International Publication No. WO 95/19179 (PCT/US95/00498), and further as described for BPI-derived peptides in U.S. Pat. No. 5,858,974, which is in turn a continuation-in-part of U.S. application Ser. No. 08/504,841 and corresponding International Publication Nos. WO 96/08509 (PCT/US95/09262) and WO 97/04008 (PCT/US96/03845), as well as in U.S. Pat. Nos. 5,733,872, 5,763,567, 5,652,332, 5,856,438 and corresponding International Publication Nos. WO 94/20532 (PCT/US/94/02465) and WO 95/19372 (PCT/US94/10427). BPI protein products exhibit anti-protozoan activity, as described in U.S. Pat. Nos. 5,646,114 and 6,013,629 and International Publication No. WO 96/01647 (PCT/US95/08624). BPI protein products exhibit anti-chlamydial activity, as described in co-owned U.S. Pat. No. 5,888,973 and WO 98/06415 (PCT/US97/13810). Finally, BPI protein products exhibit anti-mycobacterial activity, as described in co-owned, co-pending U.S. application Ser. No. 08/626,646, which is in turn a continuation of U.S. application Ser. No. 08/285,803, which is in turn a continuation-in-part of U.S. application Ser. No. 08/031,145 and corresponding International Publication No. WO 94/20129 (PCT/US94/02463).

The effects of BPI protein products in humans with endotoxin in circulation, including effects on TNF, IL-6 and endotoxin are described in U.S. Pat. Nos. 5,643,875, 5,753, 620 and 5,952,302 and corresponding International Publication No. WO 95/19784 (PCT/US95/01151).

BPI protein products are also useful for treatment of specific disease conditions, such as meningococcemia in humans (as described in U.S. Pat. Nos. 5,888,977 and 5,990,086 and International Publication No. WO97/42966 (PCT/US97/08016), hemorrhage due to trauma in humans, (as described in U.S. Pat. Nos. 5,756,464 and 5,945,399. U.S. application Ser. No. 08/862,785 and corresponding International Publication No. WO 97/44056 (PCT/US97/08941), burn injury (as described in U.S. Pat. No. 5,494,896 and corresponding International Publication No. WO 96/30037 (PCT/US96/02349)) ischemia/reperfusion injury (as described in U.S. Pat. No. 5,578,568), and depressed RES/liver resection (as described in co-owned, co-pending U.S. application Ser. No. 08/582,230 which is in turn a continuation of U.S. application Ser. No. 08/318,357, which is in turn a continuation-in-part of U.S. application Ser. No. 08/132,510, and corresponding International Publication No. WO 95/10297 (PCT/US94/11404).

BPI protein products also neutralize the anticoagulant activity of exogenous heparin, as described in U.S. Pat. No. 5,348,942, neutralize heparin in vitro as described in U.S. Pat. No. 5,854,214, and are useful for treating chronic inflammatory diseases such as rheumatoid and reactive arthritis, for inhibiting endothelial cell proliferation, and for inhibiting angiogenesis and for treating angiogenesis-associated disorders including malignant tumors, ocular retinopathy and endometriosis, as described in U.S. Pat. Nos. 5,639,727, 5,807,818 and 5,837,678 and International Publication No. WO 94/20128 (PCT/US94/02401).

BPI protein products are also useful in antithrombotic methods, as described in U.S. Pat. Nos. 5,741,779 and 5,935,930 and corresponding International Publication No. WO 97/42967 (PCT/US7/08017).

SUMMARY OF THE INVENTION

The present invention provides novel therapeutic uses for BPI protein products that involve treatment of subjects, including humans, with a BPI deficiency condition, including a selective BPI deficiency. Another aspect of the invention provides treatment of newborns, including BPI-deficient newborns, with BPI protein products. The invention is based on the discovery that the neutrophils of newborns are selectively deficient in BPI, a protein that plays an important role in defending against infection, including gram-negative bacterial infection. Treatment of subjects with a BPI deficiency condition is expected to alleviate adverse effects associated with this BPI deficiency, including, for example, decreasing susceptibility to infections, reducing the severity or invasiveness of the infection(s), and preventing the sequelae of the infection(s).

It is contemplated that the administration of a BPI protein product to a subject may be accompanied by the concurrent administration of other known therapeutic agents appropriate for treating the subject.

Use of a BPI protein product in the manufacture of a medicament for the treatment of humans with a BPI deficiency condition, including selective BPI deficiency, or a medicament for the treatment of newborns, including BPI-deficient newborns, is also contemplated.

Numerous additional aspects and advantages of the invention will become apparent to those skilled in the art upon consideration of the following detailed description of the invention which describes presently preferred embodiments thereof.

DETAILED DESCRIPTION OF THE INVENTION

The present invention provides novel therapeutic uses for BPI protein products that involve treatment of subjects with a BPI deficiency condition, including a selective BPI deficiency. Another aspect of the invention provides treatment of newborns, including BPI-deficient newborns, with BPI protein products. "Treatment" as used herein encompasses both prophylactic and therapeutic treatment.

The invention is based on the discovery that neonatal neutrophils are selectively deficient in BPI. On average, the neonatal neutrophils contained about 3-fold less BPI than the adult neutrophils, yet both groups contained nearly identical levels of other microbicidal proteins (e.g., MPO and defensin peptides) that are derived from the same primary (azurophil) granule compartment as BPI.

Although the average BPI content of newborn neutrophils was significantly lower than those of adults, it was not uniform. Some newborns apparently contain larger BPI stores than others. About 40% of newborns were markedly deficient (~9 to 10-fold less BPI than adults), with 33% of the neonatal samples showing no detectable levels of BPI at all. This variability suggests that BPI expression may be controlled by factors that are not uniformly distributed in newborns and may explain why some newborns are at greater risk of gram-negative bacterial infection than others.

The demonstration of such a BPI deficiency among newborns indicates that supplementation with BPI protein products may be of clinical benefit for newborns, including premature newborns. Newborns constitute a patient population that is at particularly high risk of infection and sepsis with subsequent poor outcomes. This demonstration of a BPI deficient condition, which has not previously been observed, also suggests that non-newborns, e.g., young children, older children or even adults, may also suffer from such a BPI deficiency and may benefit from supplementation with BPI protein products in amounts effective to alleviate the BPI deficiency. Such supplementation may provide a clinical benefit to such a BPI deficient subject. It is contemplated that supplementation is indicated whenever a BPI deficiency is observed or diagnosed, or whenever the subject is of a population with a high incidence of BPI deficiency (e.g., newborns), even if the subject is not suffering from a condition associated with gram-negative bacteria and their endotoxin, for example, gram-negative bacterial infection, endotoxemia, or sepsis.

The invention thus contemplates methods for treating a subject with a BPI deficiency condition, including selective BPI deficiency, and methods for treating newborns, including BPI-deficient newborns, which comprises administering an amount of a BPI protein product effective to alleviate the adverse effects of BPI deficiency. The treatment of premature and full-term neonates, whether healthy or suffering from congenital defects, illnesses, or infections, is contemplated.

The BPI protein product also may provide an added advantage of enhancing the subject's resistance to or ability to fight infections, including gram-negative bacterial, gram-positive bacterial and fungal infections, and prevention of the sequelae thereof. The administration of BPI protein product is expected to reduce the incidence of severe or invasive infection and to also reduce the incidence of adverse sequelae of the infection. Such sequelae include, but are not limited to, a systemic inflammatory response, endotoxemia, bacterial and/or endotoxin-related shock and one or more conditions associated therewith, fever, tachycardia, tachypnea, cytokine overstimulation, increased vascular permeability, hypotension, complement activation, disseminated intravascular coagulation, anemia, thrombocytopenia, leukopenia, pulmonary edema, adult respiratory distress syndrome, intestinal ischemia, renal insufficiency and failure, and metabolic acidosis.

"BPI-deficient newborn" means that the newborn's neutrophils contain less BPI than the neutrophils of a normal adult. Correspondingly, a "BPI deficiency condition" means a condition in which the amount of BPI measured from the subject's neutrophils is less than the amount of BPI measured from the neutrophils of a normal adult. Although the exact level of BPI for comparison purposes to determine a "deficient" level will depend on the quantitation technique used, an exemplary standard value is approximately 230 ng per $10^6$ neutrophils when a Western assay is used as described herein. Another exemplary standard value is 650 ng per $10^6$ neutrophils when a radioimmunoassay is used as described in Weiss and Olson, *Blood,* 69:652–659 (1987).

A subject with "selective BPI deficiency" means that the subject's neutrophils contain less BPI than the neutrophils of a normal adult, yet have approximately normal levels of myeloperoxidase or defensins.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. Nos. 5,198,541 and 5,641,874, the disclosures of which are incorporated herein by reference, disclose recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein, including those described in U.S. Pat. Nos. 5,198.541 and 5,641,874. Non-limiting examples of such fragments include an N-terminal fragment of natural human BPI of approximately 25 kD, described in Ooi et al., *J. Exp. Mec.,* 174:649 (1991), and the recombinant expression product of DNA encoding N-terminal amino acids from 1 to about 193 to 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra with the exceptions noted for rBPI$_{23}$ and with the exception that residue 417 is alanine (specified by GCT) rather than valine (specified by GTT). Another fragment consisting of residues 10–193 of BPI has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI fragments, as described in U.S. Pat. Nos. 5,447,913, 5,703,038, and 5,856,302 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. Nos. 5,420,019, 5,674,834 and 5,827,816 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$Δcys or rBPI$_{21}$. Production of this N-terminal analog of BPI, rBPI$_{21}$, has been described in Horwitz et al., *Protein Expression Purification*, 8:28–40 (1996). Similarly, an analog consisting of residues 10–193 of BPI in which the cysteine at position 132 is replaced with an alanine (designated "rBPI (10–193)C132A" or "rBPI(10–193)ala$^{132}$") has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI analogs; e.g. U.S. Pat. Nos. 5,447,913, 5,703,038, and 5,856,302 and corresponding International Publication No. WO 95/24209 (PCT/US95/03125), all of which are incorporated herein by reference.

Other BPI protein products useful according to the methods of the invention are peptides derived from or based on BPI produced by synthetic or recombinant means (BPI-derived peptides), such as those described in International Publication No. WO 97104008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. Nos. 5,652.332 and 5,856,438, and International Publication No. WO94/20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference. Methods of recombinant peptide production are described in U.S. Pat. No. 5,851,802 and International Publication No. WO 97/35009 (PCT/US97/05287), the disclosures of which are incorporated herein by reference.

Presently preferred BPI protein products include recombinantly-produced N-terminal analogs and fragments of BPI, especially those having a molecular weight of approximately between 20 to 25 kD such as rBPI$_{21}$ or rBPI$_{23}$, rBPI(10–193)C132A (rBPI(10–193)ala$^{132}$), dimeric forms of these N-terminal proteins (e.g., rBPI$_{42}$ dimer), and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., rBPI$_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., rBPI$_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034, 5,696,090 and 5,955,427 and corresponding International Publication No. WO 94/17819 (PCT/US94/01239), the disclosures of all of which are incorporated herein by reference. As described in U.S. Pat. No. 5,912,228 and corresponding International Publication No. WO96/21436 (PCT/US96/01095), all of which are incorporated herein by reference, other poloxamer formulations of BPI protein products with enhanced activity may be utilized, optionally with EDTA.

Therapeutic compositions comprising BPI protein product may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary (using powdered drug, or an aerosolized or nebulized drug solution), or transdermal.

When given parenterally, BPI protein product compositions are generally injected in doses ranging from 1 μg/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician. When administered intravenously, BPI protein products are preferably administered by an initial brief infusion followed by a continuous infusion. The preferred intravenous regimen is a 1 to 20 mg/kg brief intravenous infusion of BPI protein product followed by a continuous intravenous infusion at a dose of 1 to 20 mg/kg/day, continuing for up to one week. A particularly preferred intravenous dosing regimen is a 1 to 4 mg/kg initial brief intravenous infusion followed by a continuous intravenous infusion at a dose of 1 to 4 mg/kg/day, continuing for up to 72 hours.

Topical routes include administration in the form of salves, creams, jellies, ophthalmic drops or ointments (as described in co-owned, co-pending U.S. application Ser. No. 08/557,289 and Ser. No. 08/557,287, both filed Nov. 14, 1995), ear drops, suppositories, irrigation fluids (for, e.g., irrigation of wounds) or medicated shampoos. For example, for topical administration in drop form, about 10 to 200 μL of a BPI protein product composition may be applied one or more times per day as determined by the treating physician.

Those skilled in the art can readily optimize effective dosages and administration regimens for therapeutic compositions comprising BPI protein product, as determined by good medical practice and the clinical condition of the individual subject.

"Concurrent administration," or "co-administration," as used herein includes administration of the agents, in conjunction or combination, together, or before or after each other. The BPI protein product and second agent(s) may be administered by different routes. For example, the BPI protein product may be administered intravenously while the second agent(s) is(are) administered intravenously, intramuscularly, subcutaneously, orally or intraperitoneally. The BPI protein product and second agent(s) may be given sequentially in the same intravenous line or may be given in different intravenous lines. Alternatively, the BPI protein product may be administered in a special form for gastric delivery, while the second agent(s) is(are) administered, e.g., orally. The formulated BPI protein product and second agent(s) may be administered simultaneously or sequentially, as long as they are given in a manner sufficient to allow all agents to achieve effective concentrations at the site of action.

Other aspects and advantages of the present invention will be understood upon consideration of the following illustrative examples, which compare the components of neutrophils from full term neonates and from adults. Example 1 addresses the relative BPI content of neonatal and adult neutrophils. Example 2 addresses the extracellular BPI levels of neonatal and adult blood. Example 3 addresses the relative MPO and defensin peptide content of neonatal and adult neutrophils. Example 4 addresses effect of BPI protein product supplementation on antibacterial and cytokine-inducing activity of neonatal cord blood.

EXAMPLE 1

Comparison of BPI Content of Neonatal and Adult Neutrophils

In order to compare the BPI content of neonatal and adult neutrophils, cell-associated BPI was measured by Western blot analysis of neutrophil detergent extracts. The neutrophil content of BPI was then estimated by visual comparison to two-fold dilutions of purified BPI, allowing quantitation of sample values.

Neonatal neutrophils were obtained from cord blood samples, which were collected immediately after cesarean section or vaginal delivery. Cord blood was collected into sterile tubes anticoagulated with sodium heparin (Becton Dickinson) and placed on ice. All samples were labeled numerically and the results kept anonymous. Adult neutrophils were obtained from peripheral blood from healthy adult volunteers.

Neutrophils were isolated from whole blood as described in Levy et al., *J. Immunol* 154: 5403–10 (1995). Anticoagulated blood was promptly (within 30–60 minutes) processed by dextran sedimentation [3% pyrogen-free dextran (United States Biochemical) diluted in Hanks Balanced Salt Solution without divalent cations, to avoid neutrophil clumping (Gibco BRL)]. Ficoll-hypaque (endotoxin-free Ficoll-Paque Plus, Pharmacia Biotech) gradient centrifugation was employed to generate a neutrophil-rich fraction. Brief hypotonic lysis (~45 sec on ice) was employed to remove red blood cells. An automated total WBC count and differential (Technion H3 RTX automated cell counter, Miles) was obtained on every sample prior to pelleting by centrifugation. White cell differential counts were often confirmed by Wright stain and manual assessment. Neutrophil viability was assessed by trypan blue exclusion. Neutrophil pellets (typically >85% pure) were frozen in Eppendorf tubes at −70° C. prior to batch analysis.

Western blots to determine relative BPI content were conducted as follows. Neutrophils were thawed and solubilized with 4×SDS-PAGE loading buffer (0.8% SDS, 0.34 (v/v) glycerol, 0.04% Bromphenol Blue, 0.02 M DTT, 0.2 Tris pH 6.8) prior to fractionation over a 10% SDS-PAGE gel (PAGE-ONE precast 10% gels, Owl Separation System). After Western transfer onto nitrocellulose (Protran BA85, pore size 0.45 μm, Schleicher & Schuell), and blocking of non-specific sites with 3% bovine serum albumin [BSA/Tris-buffered saline pH 7.4 (BTS)], BPI was detected using 0.1% (v/v) whole anti-BPI goat serum as described in Levy et al., *J Clin Invest* 94:672–682. (1994). Bound antibody was detected using: (a) 0.05% (v/v) peroxidase-conjugated protein G followed by metal-enhanced diaminobenzoic acid (DAB; Pierce), (b) 1:35,000 dilution of peroxidase-conjugated protein G as part of the SuperSignal chemiluminescent system (Pierce), or (c) 0.1% (v/v) I-125 protein G. For detection methods (b) and (c), signal was detected by exposing the blots to Kodak XAR film. This Western transfer protocol provided detection in the range of 10–200 nanograms with readily apparent differences in signal intensity between two-fold dilutions of a BPI standard, thus allowing interpolation of BPI content in test samples. Recombinant human BPI (rBPI$_{50}$) was prepared as described in Horwitz et al., *Protein Expression & Purification* 8: 28–40 (1996).

To compare analysis of BPI content by two independent techniques, a number of neutrophil samples were extracted with sulfuric acid to solubilize BPI as described in Levy et al. (1994), supra, and analyzed for BPI content by both Western blotting and a sandwich ELISA assay as described in White et al., *J Immunol Methods* 167:227–235 (1994). Similar BPI levels were obtained by both techniques, indicating that the Western blotting data are representative and relatively accurate.

Figure 1:
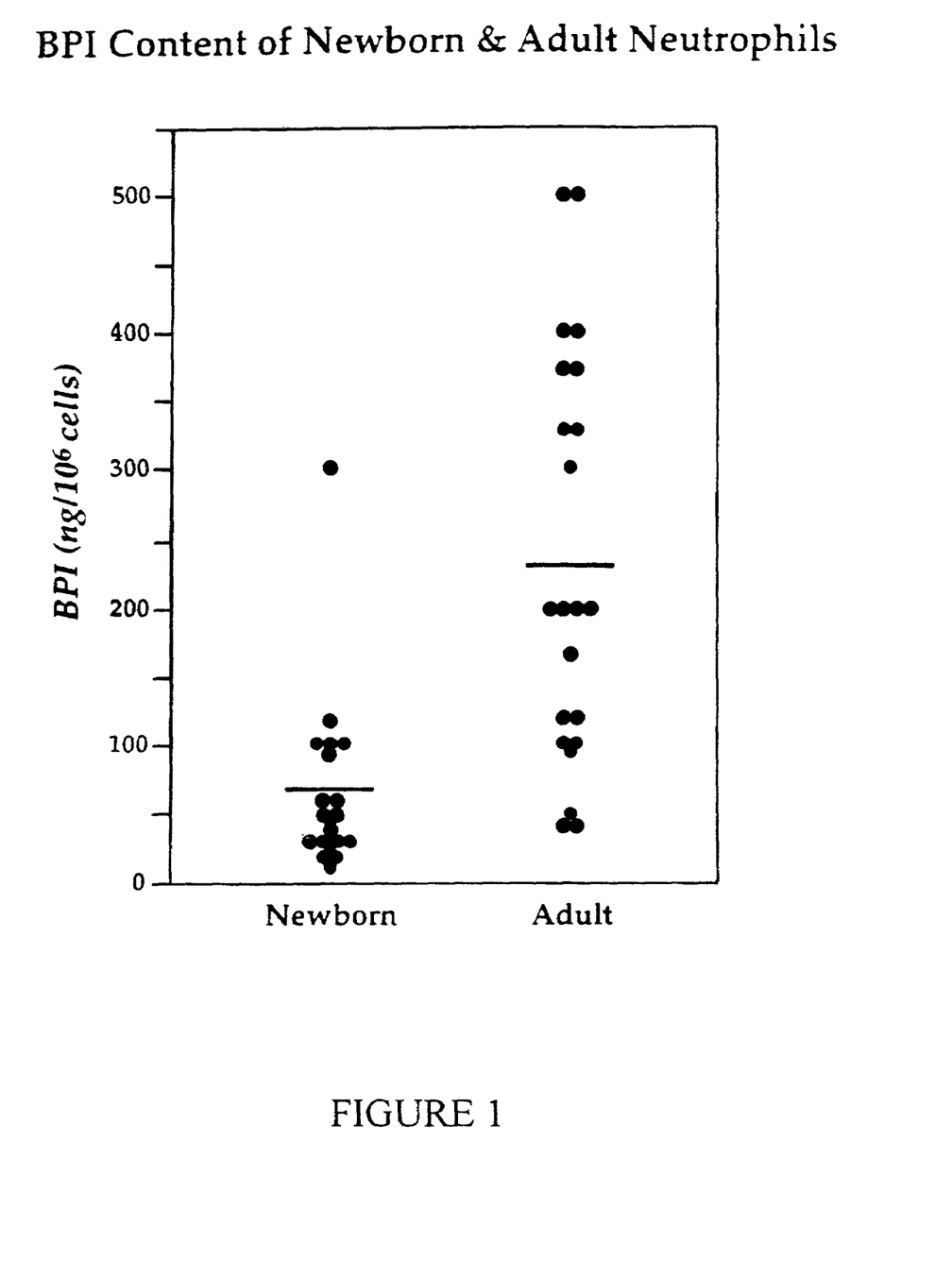
FIG. 1 displays the relative BPI content of neonatal and adult neutrophils.

Composite data from multiple Western blotting experiments are shown in FIG. 1, which is a scattergram of BPI content in the neutrophils of newborns and adults. Horizontal bars indicate average values for newborns and adults. All samples of adult neutrophils (n=22, mean age 29 years) contained quantifiable levels of BPI, the average of which was 234+/−27 ng per $10^6$ neutrophils. In contrast, newborn neutrophils (n=21, mean gestational age 38.6 weeks) contained significantly lower amounts of BPI: 67+/−13 ng per $10^6$ neutrophils ( p<0.001, 2-sided test). Median values for BPI content of adult and newborn neutrophils were 200 ng and 50 no respectively. Thus, newborn neutrophils contained at least 3-fold less BPI than adult neutrophils.

It is also evident from FIG. 1 that about 40% (8 of 21) of the newborn neutrophils were markedly deficient in BPI. Among these eight samples, seven had no detectable BPI even after prolonged exposure. This number represents 33% of the newborn patients studied. For the purposes of quantitation, such samples were considered to contain one-half of the lowest amount of BPI that was detectable in the standard curve (i.e., about 10 ng per $10^6$ neutrophils). The analysis of BPI content was thus conservatively biased towards overestimating the amount of BPI in newborn neutrophils, with the actual difference in neutrophil BPI content of some newborns relative to adults perhaps being more than 10-fold. Of note MPO was easily detected in three newborns in whom there was no detectable BPI.

EXAMPLE 2

Comparison of Extracellular Levels of BPI in Neonatal and Adult Plasma

To determine whether the relatively low BPI content of newborn neutrophils was related to degranulation, possibly secondary to perinatal stress, the levels of extracellular BPI in newborn plasma samples and adult plasma samples were compared. Newborn and adult plasma samples were collected within 30–60 minutes of drawing cord or peripheral venous blood, respectively. Samples were stored in cryogenic microtubes (Sarstedt) at −70° C. prior to batch analysis.

BPI content of plasma was determined employing a biotinylated anti-BPI antibody in a sandwich ELISA format as described in White et al. (1994), supra. This ELISA system yielded a linear range from 0.1 to 6 ng BPI/ml and showed negligible cross reactivity with the homologous lipopolysaccharide-binding protein (LBP).

The average cord plasma BPI content was 16+/−3 ng/ml (n=13), which is higher than that previously reported for plasma samples collected from 20 healthy adults (<0.2 to 2.1 ng/ml; White et al. (1994), supra). However, calculated per cc of whole cord blood, this plasma content of BPI represents less than 2% of cellular BPI content. Thus, there was no evidence for substantial extracellular degranulation of BPI at the time immediately preceding collection and processing of newborn cord blood.

EXAMPLE 3

Comparison of MPO and Defensin Levels in Neonatal and Adult Neutrophils

To assess whether other primary (azurophil) granule constituents were also relatively decreased in newborn neutrophils, the content of myeloperoxidase (MPO) and of defensin peptides in neonatal and adult neutrophils was measured as follows.

Levels of myeloperoxidase (MPO) were detected by Western blotting using 0.1% (v/v) rabbit anti-MPO serum [described in Nauseef et al., *J Clin Invest* 71: 1297–1307 (1983)] followed by 0.1% (v/v) $I^{125}$ protein G. As control for MPO blots, a two-fold dose curve of adult azurophil granule fraction (prepared as described in Borregaard et al., *J Cell Biol* 97: 52–61 (1983) was solubilized in 4×SDS-PAGE buffer and analyzed as well. For purposes of quantitation, MPO content in neutrophil samples was expressed in "antigenic units" defined in relation to an adult azurophil granule extract standard: one antigenic unit was set equal to the band intensity of an azurophil granule extract sample representing $10^6$ adult neutrophil equivalents.

Levels of defensins were detected by subjecting neutrophil extracts from adults and newborns to acid-urea (AU)-PAGE as described in Harwig et al., *Meth Enzymol* 236: 160–172 (1994). Briefly, neutrophils were sonicated in 5% acetic acid prior to overnight extraction at 4° C. Insoluble components were removed by centrifugation, supernatants lyophilized, and resuspended in AU-PAGE buffer prior to electrophoresis and Coomassie Brilliant Blue R stain. For each samples, the intensity of staining was visually compared to two-fold dilutions of control extracts.

The results of Western blotting for MPO showed that the MPO content of newborn neutrophils (6.0+/−2.5 antigenic units per $10^6$ cells, n=7 samples) and of adult neutrophils (4.3+/−1.6 antigenic units per $10^6$ cells, n=7 samples) was not statistically different. Thus, in accordance with previous observations by others (Kjeldsen et al., *Pediatr Res* 40: 120–129 (1996), newborn and adult neutrophils appear to contain nearly identical amounts of MPO.

Despite the use of a sensitive detection technique which easily revealed two-fold differences in defensin content, the AU-PAGE results for the defensin peptides showed that there was no discernible difference in the content of defensins in adult (n=8) and newborn (n=8) neutrophils. Of note, although the levels of lysozyne were somewhat decreased in some of the newborn neutroplil samples, the overall pattern of neutrophil proteins did not significantly vary in migration or band intensity between newborn and adults.

Taken together, the results in Examples 1, 2 and 3 indicate that newborn neutrophils have intrinsically lesser quantities of BPI because: (a) a priori considerations would predict that BPI should remain intracellularly since it resides in the primary (azurophilic) granules which are known to be the least easily mobilized compartment of both adult and newborn neutrophils, (b) newborn and adult neutrophils contain nearly identical amounts of both MPO and defensin, both of which are components of the same primary (azurophil) granule where BPI is stored, and it is highly unlikely that selective degranulation of BPI occurred, and (c) levels of BPI in cord plasma represent only a small fraction (<2%) of total cellular BPI, suggesting that there was no significant release of BPI from cellular stores to the extracellular space at the time immediately preceding cord blood collection.

EXAMPLE 4

Effect of BPI Protein Product Supplementation on Antibacterial Activity of Newborn Cord Blood This experiment evaluated the effect of supplementation of exogenous BPI protein product to newborn cord blood, as measured by effect on survival and TNF-α cytokine-inducing activity of various gram-negative bacteria. Cord blood samples were collected immediately after vaginal delivery (n=17) or cesarean section (n=26) into sterile tubes anticoagulated with sodium citrate [sodium citrate (0.129M, 3.8%) tubes, Becton Dickinson (Franklin Lakes, N.J.)].

The bacteria tested were *E. coli* K1/r, a K1-encapsulated, rough LPS, serum-resistant clinical isolate which has been shown to be sensitive to BPI-mediated killing both in artificial media and whole adult blood ex vivo; *Citrobacter koserii*, isolated from the blood and cerebrospinal fluid of a 14 day old male with meningitis; and *Klebsiella pneumoniae, Enterobacter agglomerans* and *Enterobacter cloaceae*, as well as *Serratia marcescens* isolated from blood cultures of newborns (7–27 day old) with congenital cardiac defects requiring invasive surgery. Frozen stocks of bacteria were prepared by culturing in trypticase soy broth [TSB, Becton Dickinson & Co., Cockeysville, Md.], and adding sterile glycerol to 15% (vol/vol) prior to freezing at −80° C.

For bactericidal assays, subcultures of bacterial stocks were prepared by inoculating a loopful into 20 ml of TSB and incubating at 37° C. with shaking for about 4 hours (to late logarithmic phase growth). Bacterial concentration was determined by measuring optical density (OD) at 550 nm in a spectrophotometer. Subcultures were harvested by centrifugation and resuspended in sterile physiologic saline to the desired concentration. Antibacterial assays were conducted in Eppendorf tubes [Research Products International (Mount Prospect, Ill.)] in a total volume of 100 μl. Samples contained 80 μl cord blood or buffered saline (20 mM sodium phosphate pH 7.4/0.9% NaCl) as a control, 10 μl rBPI$_{21}$ (or buffered saline), and 10 μl of bacteria (added last, to a final concentration of about $10^4$/ml). Samples were incubated with shaking at 37° C. At 0, 30, 90, and 180 minutes, 10 μl of each sample was plated on a Petri dish and dispersed with about 9 mL of molten (~50° C.) Bactoagar containing 0.8% (wt/vol) nutrient broth [Difco Laboratories (Detroit, Mich.)] and 0.5% (wt/vol) NaCl. The agar was allowed to solidify at room temperature, and bacterial viability was measured as the number of colonies formed after incubation of plates at 37° C. for 18 to 24 hours. Bacterial viability was expressed as colony forming units (CFU) as a percentage of the buffered saline control sample.

For cytokine-induction assays, bacteria were incubated in blood for 5 hours to allow accumulation of TNF-α. Blood was diluted five-fold with RPMI [Gibco BRL, Grand Island, N.Y.] then centrifuged at 1000×g for 5 min to collect the extracellular fluid (diluted plasma). Samples were stored frozen at 80° C. prior to measurement of TNF-α using a Quantikine TNF-α ELISA Kit [R&D System (Minneapolis, Minn.)] according to the manufacturer's instructions.

Results showed that while growth of *E. coli* K1/r was inhibited by adult blood, newborn cord blood served as a growth medium for this organism which grew logarithmically over several hours. Addition of rBPI$_{21}$ was able to markedly diminish growth of this organism both in adult and newborn cord blood with an IC$_{50}$ of about 10 nM. Similarly, growth of *Citrobacter koserii* was inhibited by adult blood but the organism grew logarithmically in newborn cord blood. Addition of rBPI$_{21}$ provided a reduction in bacterial growth with an IC$_{50}$ of about 1000 nM. *K pneumoniae, E. cloaceae* and *S. marcescens* were relatively resistant to BPI protein product, while *E. agglomerans* was too rapidly killed by both adult and newborn cord to observe an effect of BPI protein product.

Cytokine responses of newborn cord blood to *E. coli* K1/r were similar to those of adult blood. Addition of rBPI$_{21}$ was able to inhibit bacteria-induced TNF-α release with similar potency in both adult and newborn cord blood (IC$_{50}$ about 10–100 nM). *C koserii, K. pneumoniae, E. cloaceae* and *agglomerais*, and *S. marcescens* also induced substantial TNF-α release in both adult and newborn cord blood. The overall average TNF-α release induced by all of the six gram-negative isolates tested was closely similar in both adult and newborn cord blood. Addition of rBPI$_{21}$ was able to inhibit induction of TNF-α release by all of the species tested (IC$_{50}$ ranging from about 1 to 1000 nM; *C. koserii* about 100 nM, *K. pneumoniae* about 10–100 nM, *E. cloaceae* about 100 nM, *E. agglomerans* about 10–100 nM and *S. marcescens* about 1–10 nM).

Thus, these results demonstrated that replenishment of BPI in the form of rBPI$_{21}$ enhanced the antibacterial activity of newborn cord blood against *E. coli* K1/r and *C. koserii* and inhibited bacteria-induced cytokine release.

Numerous modifications and variations of the above-described invention are expected to occur to those of skill in the art. Accordingly, only such limitations as appear in the appended claims should be placed thereon.

What is claimed is:

1. A method of treating a subject with a BPI deficiency condition comprising administering to said subject a BPI protein product concurrently with a second therapeutic agent in an amount effective to alleviate the BPI deficiency.

2. The method of claim 1 wherein the subject is an adult.

3. The method of claim 1 wherein the condition is a selective BPI deficiency.

4. The method of claim 1 wherein the subject is a newborn.

5. The method of claim 4 wherein the newborn is a premature newborn.

6. The method of claim 1 wherein the BPI protein product is $rBPI_{21}$.

7. The method of claim 1 wherein the BPI protein product is an N-terminal fragment of BPI having a molecular weight approximately between about 20 to 25 kd.

8. The method of claim 1 wherein the BPI protein product is $rBPI(10-193)ala^{132}$.

9. The method of claim 1 wherein the BPI protein product is $rBPI_{50}$.

10. A method of treating a subject with a BPI deficiency condition comprising administering to said subject an amount of BPI protein product in a pharmaceutically acceptable carrier effective to alleviate the BPI deficiency.

11. The method of claim 10 wherein the pharmaceutically acceptable carrier is citrate buffered saline.

12. The method of claim 10 wherein the BPI protein product is administered systemically.

13. The method of claim 12 wherein the BPI protein product is administered orally.

14. The method of claim 12 wherein the BPI protein product is administered intravenously.

15. The method of claim 12 wherein the BPI protein product is administered intramuscularly.

16. The method of claim 12 wherein the BPI protein product is administered subcutaneously.

17. The method of claim 12 wherein the BPI protein product is administered transdermally.

18. The method of claim 12 wherein the BPI protein product is administered intrapulmonarily.

19. The method of claim 12 wherein the BPI protein product is administered intraperitonealy.

20. The method of claim 12 wherein the BPI protein product is administered intrathecally.

21. The method of claim 12 wherein the BPI protein product is administered intraocularly.

22. The method of claim 10 wherein the BPI protein product is administered topically.

* * * * *